United States Patent
Ahsani Ghahreman et al.

(10) Patent No.: US 10,045,892 B2
(45) Date of Patent: Aug. 14, 2018

(54) WOUND CARE PRODUCT

(71) Applicant: Mölnlycke Health Care AB, Göteborg (SE)

(72) Inventors: Sami Ahsani Ghahreman, Göteborg (SE); Anders Dahlberg, Olofstorp (SE); Linda Irelind, Göteborg (SE); Olof Mellbring, Floda (SE)

(73) Assignee: MÖLNLYCKE HEALTH CARE AB, Göteborg (DE)

( * ) Notice: Subject to any disclaimer, the term of this patent is extended or adjusted under 35 U.S.C. 154(b) by 0 days.

(21) Appl. No.: 15/318,488

(22) PCT Filed: May 7, 2015

(86) PCT No.: PCT/EP2015/060058
§ 371 (c)(1),
(2) Date: Dec. 13, 2016

(87) PCT Pub. No.: WO2015/197244
PCT Pub. Date: Dec. 30, 2015

(65) Prior Publication Data
US 2017/0151107 A1 Jun. 1, 2017

(30) Foreign Application Priority Data
Jun. 24, 2014 (EP) .................................. 14173600

(51) Int. Cl.
*A61L 15/00* (2006.01)
*A61F 15/00* (2006.01)
(Continued)

(52) U.S. Cl.
CPC ...... *A61F 15/001* (2013.01); *A61F 13/00076* (2013.01); *A61F 13/0203* (2013.01); *A61F 13/0253* (2013.01); *A61F 13/0259* (2013.01)

(58) Field of Classification Search
CPC ................ A61F 15/001; A61F 13/0253; A61F 13/00076; A61F 13/0203; A61F 13/0259; A61F 15/002; A61F 13/0008
(Continued)

(56) References Cited

U.S. PATENT DOCUMENTS 917,694 A * 4/1909 Wilson ................ A61F 13/0203
206/440
1,852,040 A * 4/1932 Blank ................ A61F 13/0273
206/440
(Continued)

FOREIGN PATENT DOCUMENTS

WO WO 2015/197244 12/2015

OTHER PUBLICATIONS

International Search Report dated Jul. 28, 2015 by the International Searching Authority for Application No. PCT/EP2015/060058 which was filed on May 7, 2015 and published as WO2015/197244 on Dec. 30, 2015 (Applicant—Mölnlycke Health Care AB) (4 pages).
(Continued)

*Primary Examiner* — Jacob K Ackun
*Assistant Examiner* — Jenine Pagan
(74) *Attorney, Agent, or Firm* — Ballard Spahr LLP

(57) ABSTRACT

A wound care product is provided. It comprises a sealed chamber in which a wound care article is arranged around a support member in such a manner that a curved portion of the wound care article is in contact with the support member. The curved portion interconnects two other portions on opposite sides of the support member.

13 Claims, 3 Drawing Sheets

(51) Int. Cl.
*A61F 13/02* (2006.01)
*A61F 13/00* (2006.01)

(58) Field of Classification Search
USPC ....... 206/570, 225, 438, 440, 441, 439, 494, 206/227, 495
See application file for complete search history.

(56) References Cited

U.S. PATENT DOCUMENTS

| | | | | |
|---|---|---|---|---|
| 3,520,306 A | * | 7/1970 | Gardner | A61B 17/085 602/58 |
| 3,869,044 A | * | 3/1975 | Olsson | A61B 17/06138 206/227 |
| 3,938,659 A | * | 2/1976 | Wardwell | B65D 75/5855 206/439 |
| 4,197,947 A | * | 4/1980 | Zaidi | A61L 2/26 206/438 |
| 4,549,649 A | * | 10/1985 | Roshdy | A61B 17/06133 206/380 |
| 4,655,209 A | * | 4/1987 | Scott | A61F 13/0008 206/441 |
| 5,269,421 A | * | 12/1993 | Taylor | B65D 85/672 206/411 |
| 5,986,165 A | * | 11/1999 | Moder | A61F 13/55185 604/358 |
| 6,380,455 B1 | * | 4/2002 | Moder | A61F 13/55185 206/440 |
| 2007/0287979 A1 | | 12/2007 | Kawakami et al. | |
| 2012/0031793 A1 | | 2/2012 | Watson, Jr. et al. | |
| 2012/0292426 A1 | | 11/2012 | Arefieg | |
| 2013/0146497 A1 | | 6/2013 | Tsujimura et al. | |

OTHER PUBLICATIONS

Written Opinion dated Jul. 28, 2015 by the International Searching Authority for Application No. PCT/EP2015/060058 which was filed on May 7, 2015 and published as WO2015/197244 on Dec. 30, 2015 (Applicant—Mölnlycke Health Care AB) (6 pages).

* cited by examiner

WOUND CARE PRODUCT

CROSS-REFERENCE TO RELATED APPLICATIONS

The present application is a U.S. National Phase Application of International Application No. PCT/EP2015/060058, filed May 7, 2015, which claims priority to European Patent Application No. 14173600.9, filed Jun. 24, 2014, each of which are hereby incorporated by reference in their entirety.

TECHNICAL FIELD

The present invention relates to a wound care product, comprising at least one wound care article which comprises a wound contact layer.

BACKGROUND ART

In hospitals and other nursing facilities, wound care articles comprising a wound contact layer are commonly used for treating existing wounds or as a preventive measure on intact skin for reducing the risk of new discomforts, such as e.g. preventing pressure ulcers.

Depending on the size of the wound or the area of the patient to be protected by the wound contact layer, the nursing personnel can select a wound care article of appropriate size among the different available sizes.

Small-sized wound care articles are normally applied to the wound as provided by the manufacturer. However, for larger wounds or to protect a larger area of the skin, such as when preventing skin lesions as an outcome of radiotherapy treatment, the hospital personnel commonly modifies the shape of large-sized wound care articles to fit the area of application. For instance, the large-sized wound care article may be cut into a shape which the personnel considers particularly suitable for a certain part of the human body, or may be shaped in view of some patient-specific considerations. Due to the bulkiness of large-sized wound care articles, the packages in which they are contained also tend to become large, which may be impractical from a storage and/or transportation perspective.

Thus, it would be desirable to provide a large wound care article which gives the personnel a continued freedom of customizing the shape of the wound care article, as well as being practical from a storage and/or transportation handling perspective.

SUMMARY OF THE INVENTION

An object of the present invention is to alleviate the drawbacks mentioned above. This and other objects, which will become apparent in the following are accomplished by a wound care product as defined in the accompanying independent claim.

The present invention is based on the insight that wound care articles of the type which are normally considered to be large-sized may be folded in a manner which maintains the structural integrity of the wound care article. It has furthermore been realized that this may be used for providing a wound care product which is relatively easy to store and transport, while maintaining its user-friendliness and versatility, such as allowing nursing personnel to freely customize the wound care article to a patient-specific situation.

According to an aspect of the present inventive concept, a wound care product is provided. The product comprises:

a sealed chamber,
at least one wound care article contained in said chamber,
a support member contained in the chamber for supporting the wound care article,
wherein said wound care article comprises a first portion and a second portion which are interconnected by a curved third portion of the wound care article,
wherein said wound care article is provided as a wrapping around said support member, wherein at least a part of said curved third portion is in contact with said support member.

Thus, by placing a support member in the sealed chamber and providing the wound care article at least partly around the support member, the risk of collapsing of the wound care article is counteracted, or at least reduced. For instance, when several products are piled on top of each other, the pressure on the lowermost products will be at least somewhat counteracted.

It should be understood that the expression "a wrapping around said support member" does not necessarily mean that the support member is enclosed from all sides by the wound care article. It is also not necessary for the wound care article to completely encircle the support member along its circumference. On the contrary, the wound care article being provided as wrapping around the support member, should rather be understood as at least partly enclosing, for instance like an open clam. Of course, a wrapping in the form of a complete enclosure, is also conceivable.

A normally planar wound care article may thus be arranged as an open C or U shaped wrapping around the support member, or even as a completely encircling wrapping. By providing the wound care article in such manner that it forms one or more curved portions, the risk of unwanted creases is reduced, even if the product is subjected to some pressure during storage, transportation or handling. For instance, if the wound care article comprises a wound contact layer, the risk of unwanted creases in the wound contact layer may be reduced. This is beneficial since the customizability may then be maintained. A crease in the wound contact layer might otherwise affect the nursing personnel's choice of how to cut the wound care article into an appropriate shape. The inventive solution will provide a small package and still have the advantages of freely allowing the personnel to customize it, by cutting it into desired shapes.

It should be noted, that while it on the one hand is beneficial that no creases or wrinkles are present in the wound contact layer, it may on the other hand be beneficial if other parts of the wound care article are provided with creases. For instance, a release liner may advantageously be provided with a crease, to provide a gripping tab for removing the release liner from the rest of the wound care article.

As mentioned above, at least part of the curved third portion is in contact with the support member. This promotes the structural stability of the product. For an exemplary embodiment in which a wound care article comprises a wound contact layer and a release liner, it may be the release liner of said curved third portion that is in contact with the support member or it may be the non-patient facing side of the wound contact layer of said curved third portion that is in contact with the support member.

Thus, in line with the above discussion, according to at least one exemplary embodiment, said wound care article comprises a wound contact layer. According to at least one exemplary embodiment said wound contact layer is free from any creases, said wound contact layer forming part of said first, second and third portions of the wound care article.

It should be understood that on the one hand, the wound care article may comprise several layers, e.g. a wound contact layer, a release layer (release liner) and/or a foam layer etc., said layers forming the thickness of the pad. On the other hand the first portion and the second portion and the curved third portion of the wound care article are suitably arranged sequentially in a length or width direction (as seen when the wound care article is unfolded from its wrapped position around the support member). Thus, each one of the layers, or at least some of the layers, of the wound care article may form part of said different portions of the wound care article.

The curved third portion of the wound care article, which interconnects the first and second portions, may have a substantially constant radius of curvature. In some embodiments, the interconnecting curved third portion may have several sub-portions with two or more different radii of curvature. According to at least one exemplary embodiment, the curved third portion of the wound care article has a radius of curvature in the range of 2-50 mm, suitably 3-40 mm, such as 4-30 mm, such as 5-20 mm, and suitably 6-10 mm. It should be understood that for a wound care article provided with a wound contact layer, said layer may have a radius of curvature in the above mentioned ranges.

The wound care article may suitably have a length and a width, the width being shorter than the length. According to at least one exemplary embodiment, the width of the wound care article is unchanged after being removed from the chamber. In other words, the curved third portion of the wound care article is curved in a direction perpendicular to the width direction of the wound care article. In other exemplary embodiments the curved third portion may be folded in a direction perpendicular to the length direction of the wound care article.

Depending on the size of the wound care article and the desired dimensions of the entire wound care product, a suitably dimensioned support member may be selected. In some embodiments, the wound care article may be placed in the chamber with only one curved portion. The wound care article may in such cases have a substantially U-shaped cross-section. In other words, the first and second portions would constitute the legs of the U, while the third portion would constitute the curved bottom of the U. Suitably, when the wound care article is removed from the chamber, the wound care article may assume a substantially planar shape.

In some embodiments, in particular for even longer wound care articles, it may extend further along a circumference of the support member. For instance, in some embodiments, the wound care article may be provided around the support member so that it encircles the support member.

Thus, according to at least one exemplary embodiment, the wound care article further comprises a fourth portion and a curved fifth portion, wherein said second portion and said fourth portion are interconnected by said curved fifth portion, wherein at least a part of said curved fifth portion is in contact with said support member.

In some embodiments, the curved fifth portion may be provided with substantially the same properties as the curved third portion. For instance, it may have a corresponding radius of curvature, or corresponding number of curved sub-portions with corresponding radius of curvature. In other embodiments the curved fifth portion may be provided differently compared to the curved third portion. For instance, one or more dimensions may differ.

Although in some embodiments, the curved third portion and the curved fifth portion may be arranged asymmetrically around the support member, in other embodiments, the curved third portion and the curved fifth portion, and optionally further curved portion(s), are suitably arranged symmetrically around the support member. For instance, the curved third portion and the curved fifth portion may, in some embodiments be arranged on opposite sides of the support member. Such opposite sides of the support member may, for instance, be opposite short sides of the support member, in which case the first, second and fourth portion may extend along long sides of the support member.

According to at least one exemplary embodiment, said fourth portion of the wound care article at least partly overlaps said first portion of the wound care article. This would encircle the support member.

In other embodiments, the fourth portion and the curved fifth portion may be arranged to provide a non-encircling arrangement around the support member. For instance, the wound care article may be arranged on the support member as an S-shaped cross section. For instance, the support member may be shaped as a pair of jaws, which is intertwined with the different portions of the wound care article.

The support member may be provided in different configurations and of different material as long as it can support the wound care article in the desired manner, with the third portion providing a curved transition between the first and the second portions of the wound care article. In some embodiments, the support member has a relatively long first side wall (for instance an upper side wall or front side wall) and a relatively long second side wall (for instance a lower side wall or back side wall), which may be interconnected by relatively shorter side wall portions. One or both of said side first and second walls may be provided as split side wall sections. For instance, the first side wall may have one wall section which is separated by a gap from another wall section, but which together can be regarded as forming said first side wall. An example of such a formation would be if the support member is formed from a planar sheet or blank, the opposite end portions of which are folded back towards each other. Suitably, at least one of said first and second side walls is substantially planar. However, in some embodiments, at least one of the side walls may be curved. The first side wall is, suitably spaced apart from the second side wall. However, in some embodiments, at least a portion of the first side wall may be in contact with a portion of the second side wall. For instance, the first side wall, or at least a section thereof may be non-parallel with second side wall, such that the first side wall or a section thereof converges towards the second side wall. Thus, in some embodiments, the support member may have a cross-section which comprises at least one substantially triangular shape (or the shape of a circle sector).

In some embodiments the support member may have a substantially oval or elliptical cross-section. In other embodiments, it may have a substantially rectangular cross section, suitably with the short sides of the rectangle being deformed from being completely straight to being curved or having a number of straight subsections angled slightly relative to each other. In other embodiments, the support member may have a cross-section which comprises one or more circle segments. For instance, it may have a general C-shape, U-shape, J-shape, and/or S-shape.

However, other embodiments, such as binocular-shapes are also conceivable, for providing adequate support and allowing the curved third portion of the wound care article to substantially maintain its curvature. Thus, it should be understood that a variety of possible shapes are conceivable for providing an appropriate curvature of the wound care article. For instance, the support member could simply be shaped like a pen placed in the curvature of the wound care article, in which case a major part of the wound care article would not touch the support member. In other cases the support member could be a relatively large square piece, having a suitable radius of curvature for the curved third portion, such as a radius of curvature in the range of 2-50 mm, suitably 3-40 mm, such as 4-30 mm, such as 5-20 mm, such as 6-10 mm.

According to at least one exemplary embodiment, the entire support member is contained in the sealed chamber. Thus, no part of the support member extends beyond the boundaries of the sealed chamber. In the case of the sealed chamber being a sterilized sealed chamber which defines a sterile environment, the entire support member would also be sterile, i.e. the support member would be void of non-sterile portions.

According to at least one exemplary embodiment, the sealed chamber is formed inside a package (for instance, the package may be at least partly formed by a front layer and a back layer, although other configurations are conceivable) and the entire support member is contained within the sealed chamber defined by inner surfaces of the package.

According to at least one exemplary embodiment, the sealed chamber is formed inside a package formed by a front layer and a back layer, wherein the front layer and the back layer are joined at a seam which forms a closed loop. The closed loop will generally follow the periphery of the front layer and back layer. Thus, the closed loop does not have to be circular, but could be rectangular. For instance, if the front layer and back layer are rectangular, the joining seam will extend substantially parallel with the four edges of each layer, forming a rectangular closed loop. The seam may, in this and in any of the other embodiments described in this specification, be formed by any appropriate method, such as welding, gluing, etc.

According to at least one exemplary embodiment, said support member has a higher rigidity than the wound care article. A rigid support member counteracts folds in the wound contact layer when several wound care products are piled on top of each other.

According to at least one exemplary embodiment, said support member comprises or is made of a fibrous material, such as cardboard or corrugated cardboard. However, in other embodiments other material options are also conceivable. For instance, in some embodiments, the support member is made of or comprises a plastic material, such as a molded or foamed plastic material, such as polyethylene, polypropylene and polystyrene. In other embodiments the support member may be any combination of at least the above mentioned materials.

In some embodiments, the support member may be a second wound care article which is different from the article which it supports. For instance, the support member may be a relatively thick foam for application in a wound, which may be enclosed by the wound care article having said first, second, curved third and optional other portions. In this embodiment and in other embodiments the sealed chamber may be sterile.

Thus, in at least some exemplary embodiments, the sealed chamber may be a sterilized sealed chamber which defines a sterile environment, wherein the wound care article and the support member (and any other item contained in the chamber) are also sterilized. Thus, it should be understood that such an embodiment allows the provision of items in the wound care product that can be adjusted to fit with various purposes and all items being sterile, since they are contained in the sterile environment of the chamber.

According to at least one exemplary embodiment, the support member comprises a folded sheet, which is unfoldable when removed from the chamber. Suitably, the wound care article should/can be removed before unfolding the support member. In embodiments in which the sealed chamber is a sterilized sealed chamber, the support member is provided in the sterilized chamber will be sterile at the time of removal from the chamber, and may, for instance, be used as a surgical tray for placing other products, such as the wound care article, surgical instruments, etc.

In at least some embodiments the support member is provided with information, such as printed information. For instance, it may be provided with user instructions.

Thus, in at least one exemplary embodiment, said support member is a folded surgical tray, which is unfoldable when removed from the sterilized chamber. In other words, the support member may be unfolded when the package which forms the exterior of the wound care product is opened for enabling access to the support member and the wound care article.

It should be understood that the wound care article and the support member (e.g. in the form of an unfoldable tray) may be accompanied by at least one additional wound care item in the (sterilized or non-sterilized) chamber. For instance, such additional wound care item may be surgical wipes, wound filler dressings, such as foam and gauze, tubings for negative pressure, and dressing electrodes for electro stimulation of wounds, etc.

The foldable/unfoldable support member may, for instance, be made from a cardboard blank. It may have several fold lines, in order to provide an appropriate base to arrange the curved third portion of the wound care article around/along the support member, suitably around/along a folded part of the support member.

According to at least one exemplary embodiment, said folded sheet comprise at least two fold lines along which the sheet is folded, suitably at least three fold lines.

According to at least one exemplary embodiment, said wound contact layer comprises an adhesive coating, such as a silicone adhesive coating, wherein said wound care article further comprises at least one release liner releasably attached to the adhesive coating. If more than one release liner is arranged on the wound contact layer, at least one of the release liners may comprise a folded portion which defines a gripping tab for facilitating removal of the release lines.

Although an adhesive coating may be advantageous for adhering the wound care article to the patient, in some applications such a coating may be omitted. For instance, in at least some exemplary embodiments, the wound contact layer is a foam layer, suitably a thin foam layer. In some exemplary embodiments the wound contact layer is a plastic film, such as a polyurethane film. The plastic film may be provided with or without perforations. In some exemplary embodiments, the wound contact layer is a composite comprising the (suitably thin) foam attached to the plastic film. Although each one of these exemplary embodiments may be provided without an adhesive coating, in other exemplary embodiments an adhesive coating may be present. Thus, in at least some embodiments, the wound contact layer is a layer of foam comprising an adhesive coating. In some embodiments the wound contact layer is a plastic film (with or without perforations) comprising an adhesive coating. In some embodiments, the wound contact layer is a composite of a plastic film (with or without perforations) sandwiched between a (suitably thin) layer of foam and said adhesive coating.

According to at least one exemplary embodiment, the wound care article comprises an absorbent layer. This may for instance be a fibrous material such as carboxymethyl cellulose, chitosan and polyvinyl alcohol. The absorbent fibrous material may further be a woven or a non-woven.

Thus, according to at least one exemplary embodiment, said absorbent layer comprises a foam material, such as polyurethane foam.

According to at least one exemplary embodiment, the wound care article comprises a foam layer which functions both as a wound contact layer and as an absorbent layer. The foam layer may suitably comprise an adhesive coating, such as a silicone based adhesive coating, to adhere the wound care article to the wound and/or skin According to at least one exemplary embodiment, the sealed chamber is at least partly defined by a back layer and a gas permeable front layer releasably attached to said back layer. Although, the sealed chamber does not need to be sterilized, sterilization is a conceivable option, since the gas permeable front layer allows sterilizing gas to enter there through to provide a sterilized sealed chamber.

According to at least one exemplary embodiment, the height of the support member, in a direction extending from said back layer to said front layer, is in the range of 4-100 mm, suitably 6-80 mm, such as 8-60 mm, such as 10-40 mm, such as 12-20 mm.

According to at least one exemplary embodiment the rigidity of the support member is higher than the rigidity of at least one of said back layer and said front layer. Thus, even if several wound care products are stacked on top of each other, in which case a back layer and/or a front layer might not sufficiently withstand the weight of the other products higher up in the stack, the support member contained in the sealed chamber may still adequately support the wound care article, thereby avoiding unwanted creases being formed in the wound care article.

The front layer may be made of a paper and may suitably be, permeable to a sterilizing agent, typically a sterilizing gas, such as Ethylene Oxide. However, other sterilizing methods for embodiments of the present inventive concept are also conceivable. Sterilization can be achieved by any one or a combination of known protocols in the art, some of which are standardized and approved by regulatory bodies. Non-limiting examples of sterilization methods for wound care products include autoclaving, exposure to dry heat, exposure to ultraviolet radiation, ethylene oxide treatment, gamma irradiation, immersion in aqueous alcohol solutions (e.g., 70% or greater concentrations of ethanol), gas plasma technology, steam sterilization, and electron beam irradiation. The choice of sterilization method can be influenced by a factor such as the type of material, which may have varying abilities to withstand and/or retain desirable characteristics under different sterilization protocols. For example, some ethylene oxide treatment protocols are well suited for sterilization of polymer foam materials.

DETAILED DESCRIPTION OF THE DRAWINGS

Figure 1:
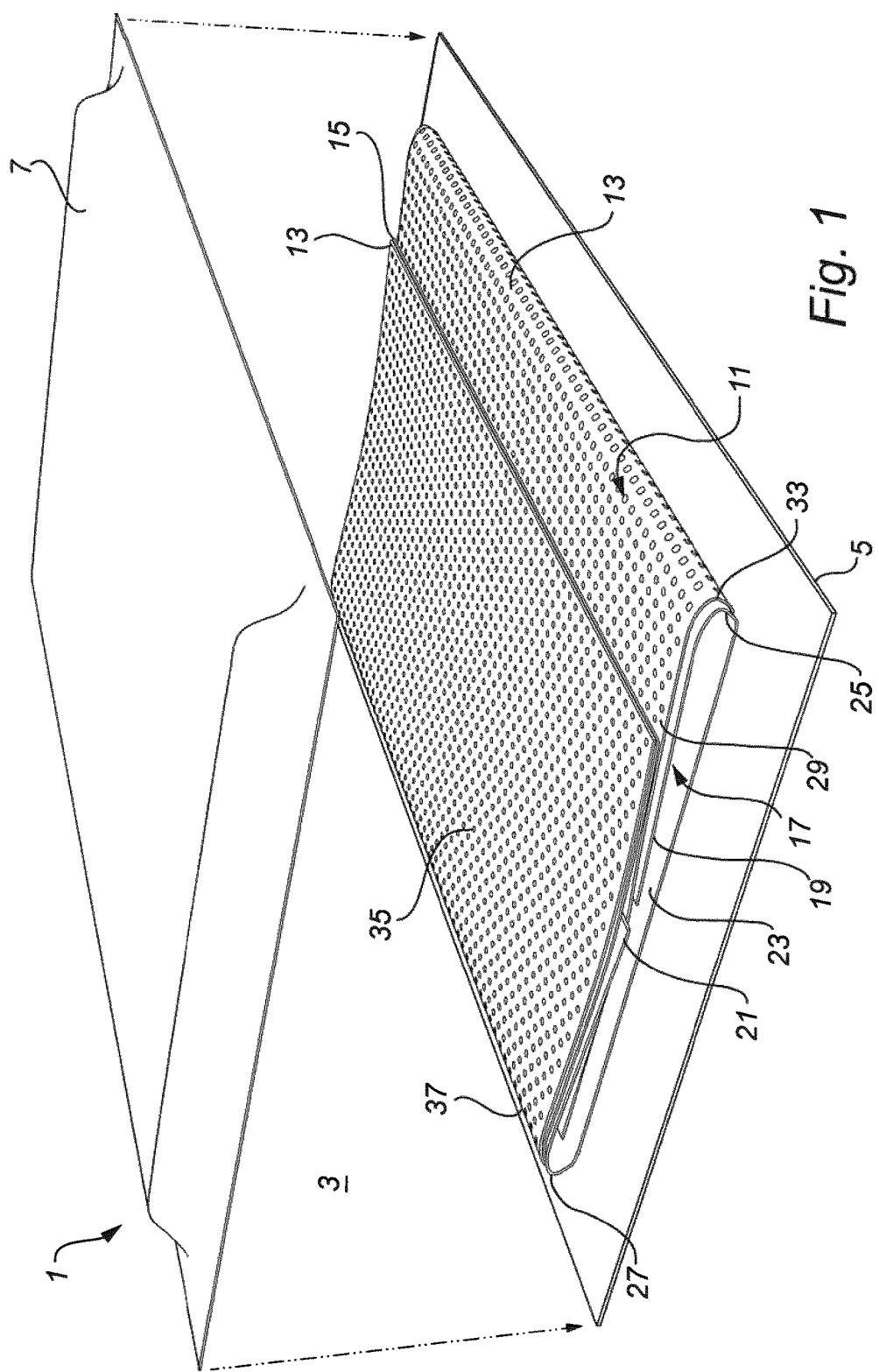
FIGS. 1-2 illustrate a wound care product according to at least one exemplary embodiment of the present inventive concept.
Figure 2:
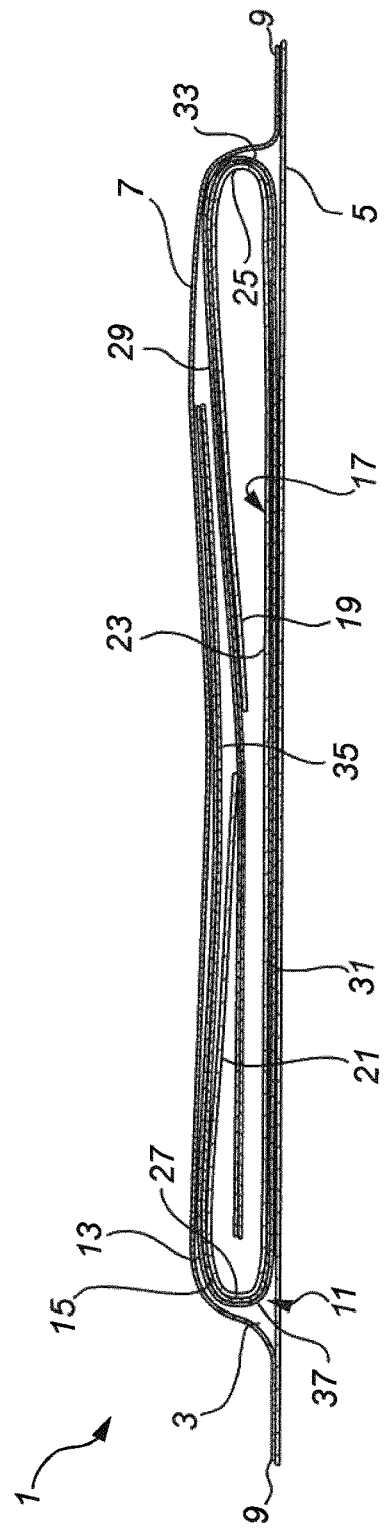

FIG. 1 is a partly exploded perspective view of at least one exemplary embodiment. FIG. 2 is a cross sectional view of said at least one embodiment.

For simplicity, the embodiments disclosed in the drawings will be described as having sterilized sealed chambers. However, it should be understood that the present inventive concept may be implemented with a non-sterilized sealed chamber or with a sterilized sealed chamber. In some applications (e.g. skin protection and ulcer prevention, in which case the wound care articles are placed on intact skin of patients) it is not necessary to have sterilized wound care articles, and therefore it should be understood that, in some embodiments, the products shown in the drawings could be provided in connection with non-sterilized sealed chambers.

Likewise it should be understood that even though terms such as "wound care article" and "wound contact layer" are used in this specification, these items are not limited to be applied only to wounds. Indeed, in at least some embodiments a wound care article and a wound contact layer may be intended for application on intact skin or for application on both intact skin and on a wound.

The wound care product 1 in FIGS. 1 and 2 is in the form of a package the interior of which presents a sterilized sealed chamber 3 which defines a sterile environment. The chamber 3 is defined by a front layer 5 and a back layer 7 sealed to the front layer 5 along the peripheral edges 9 of the two layers. Suitably, the front layer 5 is permeable to a sterilizing gas to allow for sterilization of the chamber 3 and its contents.

A sterilized wound care article 11 is contained in the chamber. The wound care article 11 comprises a wound contact layer 13 to be applied to a wound. An example of a conceivable wound contact layer is marketed by Mölnlycke Health Care under the trademark Mepitel®. At least one of the sides of the wound contact layer is coated with an adhesive (not shown). A release layer or release liner 15 is attached to the adhesive coating to prevent the wound contact layer 13 from sticking to other parts of the wound care product 1 or inadvertently getting adhered prematurely to other items. Thus, the release liner 15 is suitably removed just before applying the wound contact layer 13 onto the wound.

The sterilized chamber 3 also houses a support member 17, herein illustrated as a folded piece of cardboard. The support member 17 is made from an initially flat blank, having a length and a width. The blank is folded into five distinguishable sections. The end sections 19, 21 of the blank are folded back over a centre section 23. Each end section 19, 21 is joined to the centre section 23 via a short interconnecting section 25, 27, respectively. Each interconnecting section 25, 27 may in itself be provided with several folds to create a number of subsections which approximate a desired curved portion for the wound contact layer 13.

The end sections 19, 21, although separated from one another, can be regarded as forming a first or upper side wall of the support member 17, while the centre section 23 can be regarded as forming a second or lower side wall of the support member 17, which have been previously discussed in this disclosure. Since the support member 17 has been sterilized, it may be used as a tray on which sterile items or equipment may be placed.

In this embodiment, the wound care article 11 has been wrapped around the support member 17. A first portion 29 of the wound care article 11 (and of the wound contact layer 13) is identifiable as being located on top of one of the end sections 19 of the support member 17, and tucked in (via the gap between the end sections) underneath the other end section 21. It should be understood that the wound care article 11 may be wrapped in the illustrated way or "inside out". In other words, the release liner 15 may either be located on the inside or on the outside of the wound contact layer 13 relative to the support member 17.

In other embodiments the first portion 29 of the wound care article 11 could be arranged above both end sections 19, 21 of the support member 17. Furthermore, in other embodiments, rather than having a support member with a first or upper side wall formed by two spaced apart end sections, the support member could have a continuous first or upper side wall. Furthermore, in other embodiments rather than (as illustrated in the drawings) providing a void or space between a first or upper side wall and a second or lower side wall, the support member could be made of a sold block, or a number of connected solid blocks, without an interior space in the support member.

A second portion 31 of the care article 11 (and of the wound contact layer 13) covers the central section 23 (also referred to as a second or lower side wall). The first and second portions 29, 31 are interconnected by an integral third portion 33 of the care article (and of the wound contact layer 13). While the first and second portions 29, 31 are illustrated as being substantially planar, the third portion 33 presents a curvature. When removed from the package, the wound care article 11 and its wound contact layer 13 may be unfolded and remain structurally intact until the nursing personnel custom-cuts the wound contact layer 13.

Although, for some wound care articles it may be enough with only one rounded or curved portion (such as said third portion 33), in some embodiments such as the one illustrated in FIGS. 1 and 2, the care article 11 and the wound contact layer 13 have at least one additional curved portion. More specifically, despite the large size of the illustrated wound care article 11, it may be conveniently stored in a relatively small package while still maintaining its structural integrity and the possibility for subsequent customization by the nursing personnel.

Accordingly, in FIGS. 1 and 2, a fourth portion 35 and a curved fifth portion 37 of the care article 11 (and of the wound contact layer 13) are illustrated. The fourth portion 35 extends over the at least one of the end sections 21 of the support member 17 and, depending on its length, it may also overlap the first portion 29. The curved fifth portion 37 interconnects the second and fourth portions 31, 35, similarly to how the curved third portion 33 interconnects the first and second portions 29, 31.

Figure 3:
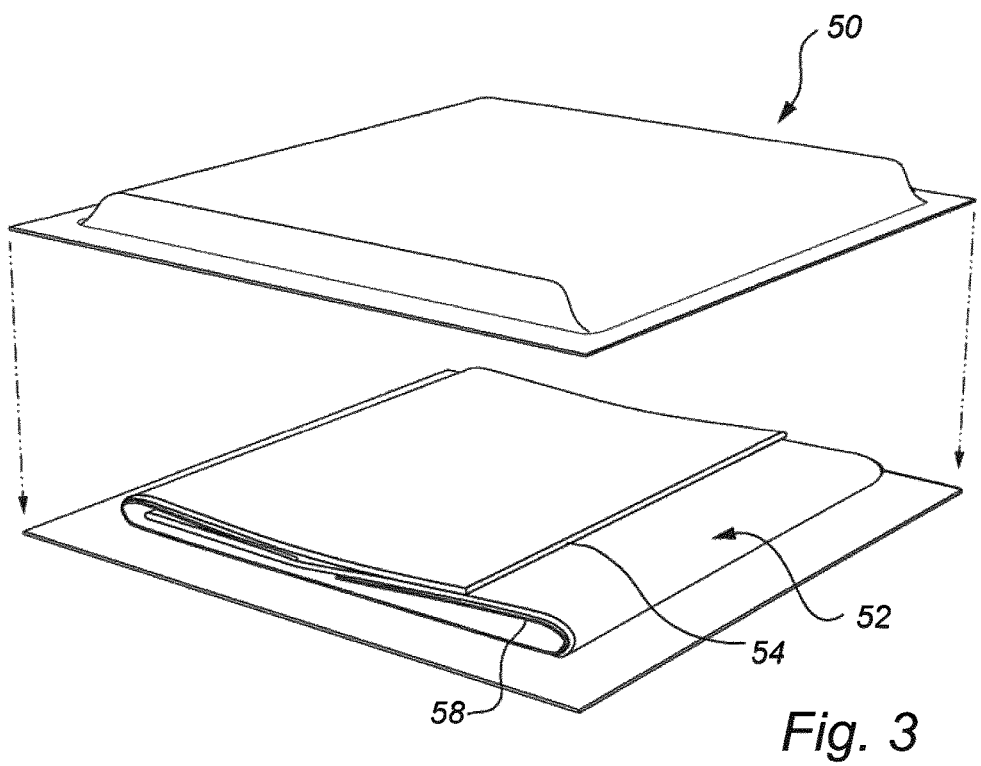
FIGS. 3-4 illustrate a wound care product according to at least another exemplary embodiment of the present inventive concept.
Figure 4:
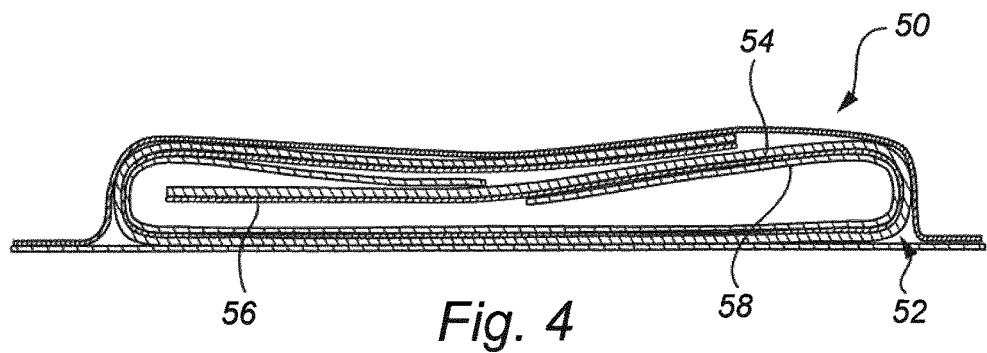

The wound care product 50 in FIGS. 3 and 4 is similar to that shown in FIGS. 1 and 2, with the exception of the wound care article 52 being different. The wound care article 52, in FIGS. 3 and 4, comprises an absorbent wound contact layer 54, such as foam, which is thicker than the wound contact layer 13 in FIGS. 1 and 2 (which could be in the form of a thin film provided with perforations). Similarly, to FIGS. 1 and 2, the wound contact layer 54 in FIGS. 3 and 4 may be provided with one or more release liners 56 covering an adhesive coating of the wound contact layer 54. Other than that, the wound care article 52 in FIGS. 3 and 4 is wrapped around a support member 58 in substantially the same manner as the wound care article 13 is wrapped around the support member 17 in FIGS. 1 and 2.

Although different exemplary embodiments have been illustrated, it should be understood that these are merely non-limiting examples. Furthermore, it should be understood that the functionality of the support member is not limited to the above examples. In particular, it is to be noted, that a support member which is included in a wound care product, may be designed in various ways within the scope of the accompanying claims, allowing a wound care article to be arranged so that extensions of one curved portion may be arranged about the support member. Such extensions (such as the previously discussed first and second portions of the wound care article) may themselves exhibit a curvature, or be substantially planar as illustrated in the drawings. Furthermore, the support member may due to its sterility, have a dual functionality, for example functioning as an item used when applying the wound contact layer to the wound. Moreover, the present inventive concept may be used with other wound care articles than those exemplified in the drawings.

The invention claimed is:

1. A wound care product, comprising
a sealed chamber,
at least one wound care article contained in said chamber,
a support member contained in the chamber for supporting said wound care article,
wherein said wound care article comprises a first portion and a second portion which are interconnected by a curved third portion of the wound care article,
wherein said wound care article is provided as a wrapping around said support member, wherein at least a part of said curved third portion is in contact with said support member,
wherein said support member has a higher rigidity than said wound care article,
wherein the support member comprises a folded sheet, which is unfoldable when removed from the sealed chamber,
wherein said sealed chamber is a sterilized sealed chamber which defines a sterile environment, wherein said wound care article is a sterile wound care article contained in said sterilized sealed chamber, and wherein said support member is a sterilized support member contained in said sterilized sealed chamber.

2. The wound care product as claimed in claim 1, wherein said wound care article comprises a wound contact layer which is free from any creases, said wound contact layer forming part of said first, second and third portions of the wound care article.

3. The wound care product as claimed in claim 1, wherein said curved third portion has a radius of curvature in the range of 2-50 mm.

4. The wound care product as claimed in claim 1, wherein said wound care article further comprises a fourth portion and a curved fifth portion, wherein said second portion and said fourth portion are interconnected by said curved fifth portion, wherein at least a part of said curved fifth portion is in contact with said support member.

5. The wound care product as claimed in claim 4, wherein said fourth portion of the wound care article at least partly overlaps said first portion of the wound care article.

6. The wound care product as claimed in claim 1, wherein the entire support member is contained in the sealed chamber.

7. The wound care product as claimed in claim 1, wherein said support member comprises cardboard.

8. The wound care product as claimed in claim 1, wherein said folded sheet comprises at least two fold lines along which the sheet is folded.

9. The wound care product as claimed in claim 2, wherein said wound contact layer comprises an adhesive coating, wherein said wound care article further comprises a release liner releasably attached to said adhesive coating.

10. The wound care product as claimed in claim 1, wherein said wound care article comprises an absorbent layer.

11. The wound care product as claimed in claim 10, wherein said absorbent layer comprises a foam material.

12. The wound care product as claimed in claim 1, wherein said sealed chamber is at least partly defined by a back layer and a gas permeable front layer releasably attached to said back layer.

13. The wound care product as claimed in claim 12, wherein the height of the support member, in a direction extending from said back layer to said front layer, is in the range of 4-100 mm.

* * * * *